United States Patent
Ma et al.

(10) Patent No.: US 12,357,301 B2
(45) Date of Patent: Jul. 15, 2025

(54) DEGRADABLE MAGNESIUM ALLOY IN-SITU COMPOSITE ANASTOMOTIC STAPLE AND A PREPARATION METHOD THEREOF

(71) Applicant: SICHUAN MEGALL MEDICAL DEVICES CO., LTD, Sichuan (CN)

(72) Inventors: Zheng Ma, Sichuan (CN); Lili Tan, Sichuan (CN); Ke Yang, Sichuan (CN)

(73) Assignee: SICHUAN MEGALL MEDICAL DEVICES CO., LTD, Chengdu (CN)

( * ) Notice: Subject to any disclaimer, the term of this patent is extended or adjusted under 35 U.S.C. 154(b) by 449 days.

(21) Appl. No.: 18/073,138

(22) Filed: Dec. 1, 2022

(65) Prior Publication Data

US 2023/0107960 A1    Apr. 6, 2023

Related U.S. Application Data

(63) Continuation-in-part of application No. PCT/CN2020/094574, filed on Jun. 5, 2020.

(51) Int. Cl.
| | |
|---|---|
| *A61B 17/06* | (2006.01) |
| *A61B 17/064* | (2006.01) |
| *A61B 17/11* | (2006.01) |
| *A61L 31/02* | (2006.01) |
| *A61L 31/14* | (2006.01) |
| *C22C 23/04* | (2006.01) |
| *A61B 17/00* | (2006.01) |

(52) U.S. Cl.
CPC .......... *A61B 17/0644* (2013.01); *A61B 17/11* (2013.01); *A61L 31/022* (2013.01); *A61L 31/148* (2013.01); *C22C 23/04* (2013.01); *A61B 2017/00964* (2013.01)

(58) Field of Classification Search
CPC .......... C22C 23/04; C22C 23/06; C22C 1/02; B21C 1/003; B21C 21/001; B21C 21/002
See application file for complete search history.

(56) References Cited

U.S. PATENT DOCUMENTS

| | | | |
|---|---|---|---|
| 2006/0198869 A1 | 9/2006 | Furst et al. | |
| 2010/0082092 A1* | 4/2010 | Gerold | C22F 1/06 623/1.15 |

FOREIGN PATENT DOCUMENTS

| | | |
|---|---|---|
| CN | 102698317 A | 10/2012 |
| CN | 106521250 A | 3/2017 |
| CN | 107736906 A | 2/2018 |
| CN | 110144534 A | 8/2019 |
| CN | 110234366 A | 9/2019 |
| CN | 111424202 A | 7/2020 |

OTHER PUBLICATIONS

International search report of PCT/CN2020/094574, mailed Mar. 10, 2021.
Fluoride Conversion Coating on Biodegradable AZ31BMagnesium Alloy Yan Tingting et al Journal of Materials Science & Technology vol. 30, No. 7,Jul. 1, 2014(Jul. 1, 2014), pp. 666-674, XP093052897, Amsterdam, NL ISSN: 1005-0302, DOI: 10.1016/j.jmst.2013.12.015.

* cited by examiner

*Primary Examiner* — Jessee R Roe

(57) ABSTRACT

The present disclosure relates to the technical field of biomedical materials, more particularly to a degradable magnesium alloy in-situ composite anastomotic staple and a preparation method thereof. The anastomotic staple, with a composite structure, is mainly composed of Mg—Zn—Nd magnesium alloy with high strength and good plasticity (internal part), and corrosion-resistant $MgF_2$ (external part), and is formed by in-situ synthesis of $MgF_2$ with the outer layer of Mg—Zn—Nd magnesium alloy anastomotic staple. The magnesium alloy composite anastomotic staple provided by the present disclosure has good plastic deformation ability and mechanical strength, a low degradation rate, and a high biosafety level, which can meet the in-vivo implantation requirements. In addition, it can gradually degrade in vivo after achieving the medical effects in vivo, avoiding a second operation for removal.

3 Claims, 1 Drawing Sheet

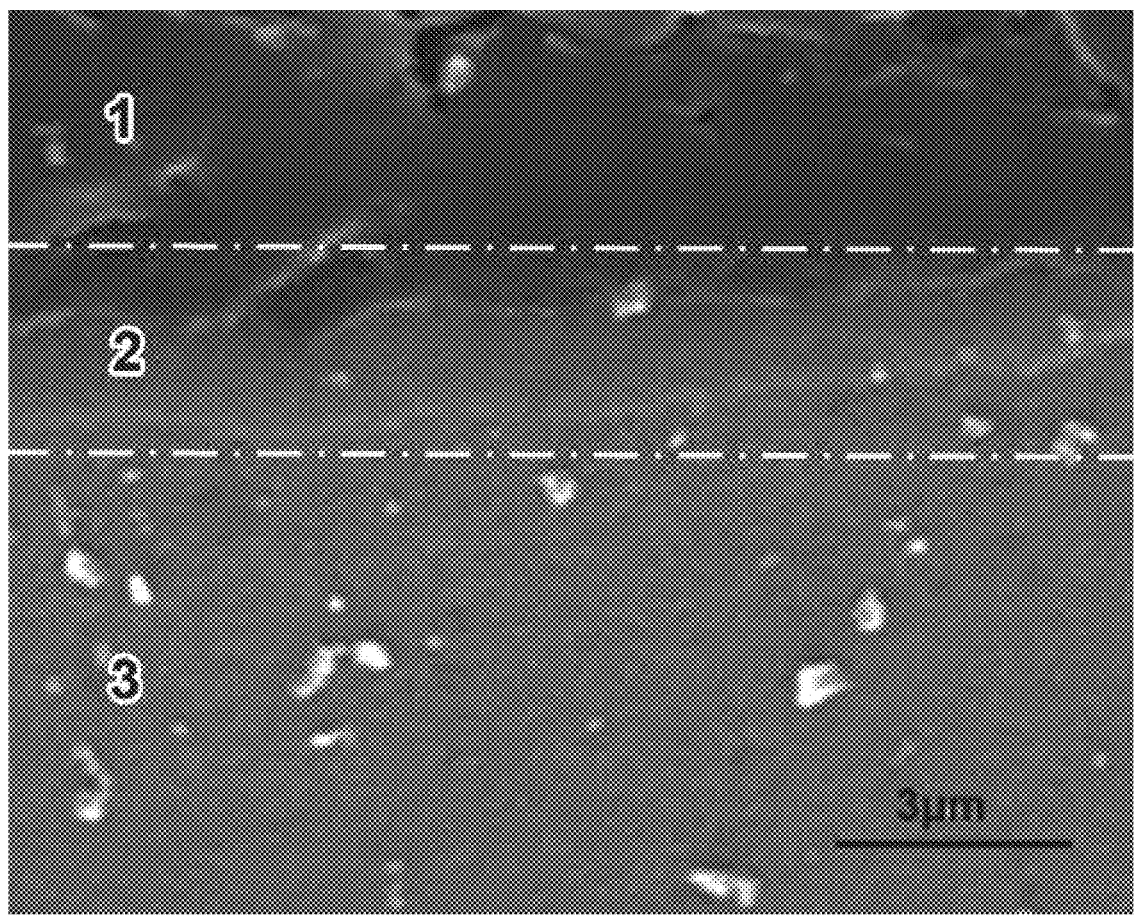

DEGRADABLE MAGNESIUM ALLOY IN-SITU COMPOSITE ANASTOMOTIC STAPLE AND A PREPARATION METHOD THEREOF

TECHNICAL FIELD

The present disclosure relates to the technical field of biomedical materials, more particularly to a degradable magnesium alloy in-situ composite anastomotic staple and a preparation method thereof.

BACKGROUND OF THE DISCLOSURE

The existing titanium alloy anastomotic staples are non-degradable and considered foreign bodies in the human body. The long-term retention of foreign bodies is prone to lead to adverse reactions such as inflammation, delayed healing, sensitization, and carcinogenesis. To remove the implanted device after tissue repair or healing, a second operation is required, resulting in additional surgical risks, economic stress, and physiological pain to patients.

Magnesium alloy is degradable and magnesium corrodes easily in human body fluid. This helps to realize the medical and clinical purpose of magnesium alloy implants gradually degrading in vivo until they eventually disappear. Compared with conventional metal implants, magnesium alloy ones need no second operation for removal, reducing the mental and economic burden on patients. However, there are still problems such as a high degradation rate, poor mechanical strength, and poor plasticity.

Patent Authorized Announcement No. CN106086562B discloses a method to prepare magnesium alloy anastomotic staples with the powder of Zn, Mn, Sn, Ag, and HA by alloying to improve the corrosion resistance and plasticity of the alloy to a certain extent. However, this preparation process is complicated and it is extremely difficult to form anastomotic staples directly by extrusion. In addition, there has been no relevant academic literature dealing on this. Patent Authorized Announcement No. CN 201617885 U improves the corrosion resistance, strength and hardness of anastomotic staples to a great extent by adding ceramic, metal and oxide coatings on the surface of anastomotic staples. However, such coatings are hard and tend to come off during the deformation and anastomosis of anastomotic staples, affecting the effects of anastomotic staples. Patent Authorized Announcement No. CN 105326535 A adds a drug coating on the surface of anastomotic staples, which has biological functions such as anti-bacterial infection, hemostasis and inhibition of vascular restenosis, but fails to solve the fundamental problem of unmatched mechanical properties with degradation rate of the degradable anastomotic staples.

SUMMARY

The present disclosure is to provide a degradable magnesium alloy in-situ composite anastomotic staple and a preparation method thereof, so as to solve the problems of high degradation rate, low mechanical strength and poor plasticity of the existing degradable magnesium alloy anastomotic staples.

The technical solution relating to the disclosure:

The present disclosure relates to a degradable magnesium alloy in-situ composite anastomotic staple. The anastomotic staple, with a composite structure, is mainly composed of Mg—Zn—Nd magnesium alloy with high strength and good plasticity (internal part), and corrosion-resistant $MgF_2$ (external part), and is formed by adding in-situ composites of $MgF_2$ onto the outer layer of Mg—Zn—Nd magnesium alloy anastomotic staple.

Based on the weight percentage of the degradable magnesium alloy in-situ composite anastomotic staple, the chemical components of the Mg—Zn—Nd magnesium alloy anastomotic staple and their contents are as follows: Zn (0.2%-3.0%), Nd (0.2%-2.3%), and Mg (the rest).

The more preferred chemical components of the Mg—Zn—Nd magnesium alloy anastomotic staple and contents are as follows: Zn (1.0%-3.0%), Nd (0.2%-1.0%), and Mg (the rest).

Based on the weight percentage of the degradable magnesium alloy in-situ composite anastomotic staple, the technical indicators of the Mg—Zn—Nd magnesium alloy anastomotic staple are as follows: the tensile strength range is 260-320 MPa, and the yield strength range is 170-240 MPa.

Among the preferred anastomotic staples of the present disclosure, the elongation of the magnesium alloy wire is in the range of 20-33%.

The thickness of $MgF_2$, which plays a role in corrosion prevention of the outer layer, is 1.0 μm-3.3 μm for the degradable magnesium alloy in-situ composite anastomotic staple.

The preparation method of a degradable magnesium alloy in-situ composite anastomotic staple comprises the following steps:

(1) Melt the pure Mg, Zn and Nd in proportion into magnesium alloy, cast it into ingots and homogenize the ingots at 300-450° C. for 3-7 h;

(2) Remove the surface defects and impurities of the magnesium alloy ingots from Step (1), and extrude them into bars with a diameter of 8-10 mm as per an extrusion ratio of 60-80:1 at a temperature of 390-470° C.;

(3) Cold-draw the magnesium alloy bars from Step (2) into wires with a diameter of 0.2-0.6 mm, and anneal them at a temperature of 280-330° C. for 30 min-120 min;

(4) Make U-shaped anastomotic staples out of the magnesium alloy wires from Step (3);

(5) Electropolish the magnesium alloy anastomotic staples from Step (4) to remove surface defects, and then ultrasonically clean and dry them;

(6) Immerse the magnesium alloy anastomotic staples from Step (5) into the hydrofluoric acid with a weight concentration of 20%-60% for in-situ synthesis with $MgF_2$ at 20-35° C. for 3 h-200 h;

(7) Ultrasonically clean and dry the in-situ composite magnesium alloy anastomotic staples from Step (6), and vacuum-seal them.

In Step (4) of the preparation method of a degradable magnesium alloy in-situ composite anastomotic staple, the bending part of the U-shaped anastomotic staple is elliptical, the total length of the anastomotic staple is 10-15 mm, the height of the anastomotic staple is 3-6 mm, and the diameter of the anastomotic staple end face is 0.20-0.35 mm.

In Step (5) of the preparation method of a degradable magnesium alloy in-situ composite anastomotic staple, fine electropolishing is carried out with the polishing solution, a mixture with the volume ratio of 2-ethoxyethanol:absolute ethanol:phosphoric acid=1:2:2, and the weight concentration of phosphoric acid of 85% for 1-10 min under the voltage of 10-20 V.

The design idea of the present disclosure:

The titanium alloy anastomotic staples currently used are non-degradable and their long-term stay in the human body tend to cause infection and other problems. The present disclosure provides a magnesium matrix composite anastomotic staple, which adopts alloying elements Zn and Nd to improve the strength and plasticity of the alloy. In view of the problem that the degradation rate of the magnesium alloy anastomotic staple is too high, the in-situ chemical synthesis technology is adopted to add composite layers of magnesium fluoride and magnesium oxide material onto the outermost layer of the magnesium matrix anastomotic staple to improve the corrosion resistance of the anastomotic staple.

The magnesium matrix composite anastomotic staple in the present disclosure is comprised of alloying elements Zn and Nd. As Zn in Mg has significant effects in solid solution strengthening and aging strengthening, it can improve the strength of the alloy, effectively increase the flexibility of the slip direction of the alloy cylindrical surface, and improve the plastic deformation ability and processing performance of the magnesium alloy. Zn, an essential microelement in the human body with a high biosafety level, is involved in the metabolism of proteins and enzymes and is closely related to the operation of the nervous system and the maintenance of immune organs. The solid solubility of Nd in magnesium is 3.6%. The drawing property and corrosion resistance of magnesium alloys can be improved by solution heat treatment, and the strength and plasticity of magnesium alloy can be improved by grain refinement. Clinical studies have shown that an appropriate amount of rare earth elements can promote the proliferation of osteoblasts, protect the nervous system, prevent coagulation, arteriosclerosis and cancers, treat diabetes mellitus, and provide anti-inflammatory and analgesic effects. Only an excessive amount of rare earth elements may cause certain adverse effects on the human body. In addition, fluoride is one of the important microelements in the human body. It can stimulate the proliferation of osteoblasts, promote mineral deposition on cancellous bone, promote iron absorption and bone and tooth growth, and improve neuronal excitability and exert good anti-aging effects. The safe and appropriate intake of fluoride is 1.5-4.0 mg for adults published by the Chinese Nutrition Society (CNS).

The advantages and beneficial effects of the present disclosure areas follows:

1. In order to solve the problems of high degradation rate, weak coating adhesion, low mechanical strength, and poor plasticity existing in degradable magnesium alloy anastomotic staples, an alloying strategy is adopted first to prepare an Mg—Zn—Nd alloy. After cold drawing and heat treatment processes, the mechanical strength and plasticity of the alloy are improved; then the in-situ synthesis of magnesium fluoride is adopted to give the designed anastomotic staple better corrosion resistance and higher biosafety level. The anastomotic staple of the present disclosure can better meet the requirements for in vivo use.
2. The anastomotic staple provided by the present disclosure has a high biosafety level, good mechanical properties and plasticity, and excellent corrosion resistance. It can meet the requirements for use of anastomotic staples and can degrade and disappear after achieving corresponding effects in vivo, avoiding a second operation for removal.
3. The magnesium matrix composite material provided by the present disclosure can improve the mechanical properties and corrosion resistance of anastomotic staples required to meet the requirements for use of medical degradable anastomotic staples.

BRIEF DESCRIPTION OF THE DRAWINGS

Solo FIGURE is an SEM micrograph of the magnesium matrix composites. Wherein, layer 2 is the in-situ composite $MgF_2$, layer 3 is the magnesium alloy matrix, and layer 1 is the epoxy resin required to prepare the sample.

DETAILED DESCRIPTION

In the detailed description of the preferred embodiment, the present disclosure provides a degradable anastomotic staple with a high biosafety level, good mechanical properties and plasticity, and excellent corrosion resistance through alloying combined with drawing and in-situ synthesis.

The embodiments of the present disclosure will be further described in detail as follows with reference to the drawings. The embodiments are implemented based on the technical solution of the disclosure with the specific implementation method and procedures given. However, the protection scope of the disclosure is not limited to the following embodiments.

Embodiment 1

In this embodiment, the anastomotic staples are prepared in the following way: melt pure magnesium, 1% Zn and 1% Nd into liquid based on weight percentage; cast the liquid metal into ingots and remove their surface defects and impurities; homogenize the ingots at 400° C. for 4 h and make magnesium alloy bars with a diameter of 10 mm (extrusion ratio of 70:1) by hot extrusion at 430° C.; cold-draw the bars to make wires with a diameter of 0.3 mm and anneal the wires at 300° C. for 60 min. Make U-shaped anastomotic staples out of magnesium alloy wires with an elliptical bending part, a total length of 10-15 mm, a height of 3-6 mm, and an end face diameter of 0.20-0.35 mm. Electropolish the anastomotic staples for 5 min under a voltage of 15 V to remove surface defects and impurities with a mixture of 2-ethoxyethanol, absolute ethanol, and phosphoric acid at a volume ratio of 1:2:2 (the weight concentration of phosphoric acid being 85%). Then ultrasonically clean and dry the anastomotic staples, and immerse them into hydrofluoric acid with a weight concentration of 35% for in-situ synthesis with magnesium fluoride at room temperature for 6 h. Finally, ultrasonically clean, dry and vacuum-seal the anastomotic staples.

Mechanical properties and cytotoxicity data of the anastomotic staples in this embodiment are presented in Table 1 and corrosion resistance data is provided in Table 2.

Embodiment 2

In this embodiment, the anastomotic staples are prepared in the following way: melt pure magnesium, 1.73% Zn and 0.68% Nd into liquid based on weight percentage; cast the liquid metal into ingots and remove their surface defects and impurities; homogenize the ingots at 380° C. for 6 h and make magnesium alloy bars with a diameter of 10 mm (extrusion ratio of 60:1) by hot extrusion at 420° C.; cold-draw the bars to make wires with a diameter of 0.3 mm and anneal the wires at 280° C. for 120 min. Make U-shaped anastomotic staples out of magnesium alloy wires with an elliptical bending part, a total length of 10-15 mm, a height of 3-6 mm, and an end face diameter of 0.20-0.35 mm.

Electropolish the anastomotic staples for 3 min under a voltage of 20 V to remove surface defects and impurities with a mixture of 2-ethoxyethanol, absolute ethanol, and phosphoric acid at a volume ratio is 1:2:2 (the weight concentration of phosphoric acid being 85%). Then ultrasonically clean and dry the anastomotic staples, and immerse them into hydrofluoric acid with a weight concentration of 40% for in-situ synthesis with magnesium fluoride at room temperature for 7 h. Finally, ultrasonically clean, dry, and vacuum-seal the anastomotic staples.

Mechanical properties and cytotoxicity data of the anastomotic staples in this embodiment are presented in Table 1 and corrosion resistance data is provided in Table 2.

Embodiment 3

In this embodiment, the anastomotic staples are prepared in the following way: melt pure magnesium, 1.6% Zn and 0.7% Nd into liquid based on weight percentage; cast the liquid metal into ingots and remove their surface defects and impurities; homogenize the ingots at 420° C. for 5 h and make magnesium alloy bars with a diameter of 10 mm (extrusion ratio of 80:1) by hot extrusion at 410° C.; cold-draw the bars to make wires with a diameter of 0.3 mm and anneal the wires at 320° C. for 30 mm. Make U-shaped anastomotic staples out of magnesium alloy wires with an elliptical bending part, a total length of 10-15 mm, a height of 3-6 mm, and an end face diameter of 0.20-0.35 mm. The anastomotic staples are electropolished to remove surface defects and impurities. The electropolishing solution used is a mixture with the volume ratio of 2-ethoxyethanol:absolute ethanol:phosphoric acid=1:2:2 and the weight concentration of phosphoric acid of 85%. The electropolishing lasts for 6 min under a voltage of 10 V. Then the anastomotic staples are ultrasonically cleaned, dried and immersed into hydrofluoric acid with a weight concentration of 45% for in-situ synthesis with magnesium fluoride at room temperature for 8 h. Finally, the anastomotic staples are ultrasonically cleaned, dried and vacuum-sealed.

Mechanical properties and cytotoxicity data of the anastomotic staples in this embodiment are presented in Table 1 and corrosion resistance data is provided in Table 2.

TABLE 1

MECHANICAL PROPERTIES AND CYTOTOXICITY OF ANASTOMOTIC STAPLES

| | Tensile Strength (MPa) | Yield Strength (MPa) | Elongation (%) | Cytotoxicity |
|---|---|---|---|---|
| EMBODIMENT1 | 310.2 | 236.2 | 25 | Grade 0 |
| EMBODIMENT2 | 296.4 | 221.6 | 27 | Grade 0 |
| EMBODIMENT3 | 314.2 | 239.7 | 29 | Grade 0 |

TABLE 2

CORROSION RESISTANCE OF ANASTOMOTIC STAPLES

| | $E_0$ (V) | $I_c$ (A/cm$^2$) | $R_p$ ($\Omega$/cm$^2$) |
|---|---|---|---|
| EMBODIMENT1 | −1.56 | $5.23 \times 10^{-7}$ | $3.65 \times 10^5$ |
| EMBODIMENT2 | −1.53 | $6.59 \times 10^{-8}$ | $5.3 \times 10^5$ |
| EMBODIMENT3 | −1.49 | $3.59 \times 10^{-8}$ | $6.8 \times 10^5$ |

From Table 1 and Table 2, it can be concluded that the anastomotic staples of the present disclosure have high tensile strength and excellent plasticity that meet the requirements for mechanical properties, and that the cytotoxicity of the anastomotic staples is Grade 0, indicating that the anastomotic staples have high cytocompatibility.

As shown in solo FIGURE, it can be seen from the SEM micrograph of magnesium matrix composites that there is no obvious delamination between the matrix of the composites and in-situ composite $MgF_2$, which is different from conventional coatings. The in-situ composite $MgF_2$ layer ensures the structural and property stability of the material, and improves the corrosion resistance of the alloy.

The embodiment results show that the magnesium alloy composite anastomotic staple provided by the present disclosure has good plastic deformation ability and mechanical strength, a low degradation rate, and a high biosafety level, which can meet the requirements of in vivo implantation. In addition, it can gradually degrade in vivo after achieving the medical effects in vivo, avoiding a second operation for removal.

Embodiment 4

In this embodiment, the anastomotic staples are prepared in the following way: melt pure magnesium, 2.0% Zn and 0.5% Nd into liquid based on weight percentage; cast the liquid metal into ingots and remove their surface defects and impurities; homogenize the ingots at 380° C. for 6 h and make magnesium alloy bars with a diameter of 10 mm (extrusion ratio of 60:1) by hot extrusion at 410° C.; cold-draw the bars to make wires with a diameter of 0.3 mm and anneal the wires at 280° C. for 120 min. Make U-shaped anastomotic staples out of magnesium alloy wires with an elliptical bending part, a total length of 10-15 mm, a height of 3-6 mm, and an end face diameter of 0.20-0.35 mm. Electropolish the anastomotic staples for 3 min under a voltage of 20 V to remove surface defects and impurities with a mixture of 2-ethoxyethanol, absolute ethanol, and phosphoric acid at a volume ratio is 1:2:2 (the weight concentration of phosphoric acid being 85%). Then ultrasonically clean and dry the anastomotic staples, and immerse them into hydrofluoric acid with a weight concentration of 40% for in-situ synthesis with magnesium fluoride at room temperature for 7 h. Finally, ultrasonically clean, dry, and vacuum-seal the anastomotic staples.

The wires used for the anastomotic staples in this embodiment have a tensile strength of 265 Mpa, a yield strength of 173 Mpa, a cytotoxicity grade of 0, and a corrosion current density of $6.18 \times 10^{-7}$, making them good materials for forming staples.

Comparative Example 5

In this embodiment, the anastomotic staples are prepared in the following way: melt pure magnesium, 6.0% Zn and 0.5% Nd into liquid based on weight percentage; cast the liquid metal into ingots and remove their surface defects and impurities; homogenize the ingots at 380° C. for 6 h and make magnesium alloy bars with a diameter of 10 mm (extrusion ratio of 60:1) by hot extrusion at 410° C.; cold-draw the bars to make wires with a diameter of 0.3 mm and anneal the wires at 280° C. for 120 min. Make U-shaped anastomotic staples out of magnesium alloy wires with an elliptical bending part, a total length of 10-15 mm, a height of 3-6 mm, and an end face diameter of 0.20-0.35 mm. Electropolish the anastomotic staples for 3 min under a voltage of 20 V to remove surface defects and impurities with a mixture of 2-ethoxyethanol, absolute ethanol, and phosphoric acid at a volume ratio is 1:2:2 (the weight concentration of phosphoric acid being 85%). Then ultrasonically clean and dry the anastomotic staples, and immerse them into hydrofluoric acid with a weight concentration of 40% for in-situ synthesis with magnesium fluoride at room temperature for 7 h. Finally, ultrasonically clean, dry, and vacuum-seal the anastomotic staples.

The wires used for the anastomotic staples in this comparative example have a tensile strength of 368 Mpa, a yield strength of 256 Mpa, an elongation of 4%, a cytotoxicity grade of 0, and a corrosion current density of $9.59 \times 10^{-7}$. It is found in this comparative example that magnesium alloy anastomotic staples are difficult to form when the wire elongation is 4%. This is mainly because of the increase of Zn content in the alloy. Although the tensile strength and yield strength of the alloy increase, its elongation drops dramatically.

Therefore, massive studies have found that the content of Zn and Nd should be controlled within a certain range in order to form staples, for example, within the following ranges: Zn 0.2%-3.0%, Nd 0.2%-2.3%, and the rest is Mg, or preferably within such ranges: Zn 1.0%-3.0%, Nd 0.2%-1.0%, and the rest is Mg. The alloy has a high strength-plasticity matching ratio and a low degradation rate and forms staples easily especially when the elongation of magnesium alloy wires ranges from 20%-33%.

What is claimed is:

1. A preparation method of a degradable magnesium alloy in-situ composite anastomotic staple, comprising the following operating steps:
   (1) melting pure Mg, Zn and Nd in proportion into magnesium alloy, casting it into ingots and homogenizing the ingots at 300-450° C. for 3-7 h;
   (2) removing the surface defects and impurities of the magnesium alloy ingots from Step (1), and extruding them into bars with a diameter of 8-10 mm as per an extrusion ratio of 60-80:1 at a temperature of 390-470° C.;
   (3) cold-drawing the magnesium alloy bars from Step (2) into wires with a diameter of 0.2-0.6 mm, and annealing them at a temperature of 280-330° C. for 30 min-120 min;
   (4) making U-shaped anastomotic staples out of the magnesium alloy wires from Step (3);
   (5) electropolishing the magnesium alloy anastomotic staples from Step (4) to remove surface defects, and then ultrasonically cleaning and drying them;
   (6) immersing the magnesium alloy anastomotic staples from Step (5) into the hydrofluoric acid with a weight concentration of 20%-60% for in-situ synthesis with $MgF_2$ at 20-35° C. for 3 h-200 h;
   (7) ultrasonically cleaning and drying the in-situ composite magnesium alloy anastomotic staples from Step (6), and vacuum-sealing them.

2. The preparation method of a degradable magnesium alloy in-situ composite anastomotic staple according to claim 1, characterized in that in Step (4), the U-shaped anastomotic staple is 10-15 mm long and 3-6 mm high with an elliptical bending part and an end face diameter of 0.20-0.35 mm.

3. The preparation method of a degradable magnesium alloy in-situ composite anastomotic staple according to claim 1, characterized in that in Step (5), fine electropolishing is carried out with the polishing solution, a mixture with the volume ratio of 2-ethoxyethanol:absolute ethanol:phosphoric acid=1:2:2, and the weight concentration of phosphoric acid of 85% for 1-10 min under the voltage of 10-20 V.

* * * * *